(12) United States Patent
Ferree

(10) Patent No.: US 8,109,978 B2
(45) Date of Patent: Feb. 7, 2012

(54) METHODS OF POSTERIOR FIXATION AND STABILIZATION OF A SPINAL SEGMENT

(75) Inventor: Bret A. Ferree, Cincinnati, OH (US)

(73) Assignee: Anova Corporation

( * ) Notice: Subject to any disclaimer, the term of this patent is extended or adjusted under 35 U.S.C. 154(b) by 1106 days.

(21) Appl. No.: 11/945,998

(22) Filed: Nov. 27, 2007

(65) Prior Publication Data

US 2008/0125780 A1    May 29, 2008

Related U.S. Application Data

(60) Provisional application No. 60/861,499, filed on Nov. 28, 2006.

(51) Int. Cl.
*A61B 17/88* (2006.01)
(52) U.S. Cl. ...................................... 606/279
(58) Field of Classification Search .............. 606/60, 606/246, 263, 279, 280, 70–71, 281, 283–286, 606/300–321, 228–232, 74, 103, 151–156; 623/17.11–17.16, 13.13–13.14
See application file for complete search history.

(56) References Cited

U.S. PATENT DOCUMENTS

| 5,725,582 | A   | * | 3/1998  | Bevan et al. ............... 606/263 |
| 6,248,106 | B1  | * | 6/2001  | Ferree ........................ 606/263 |
| 2005/0113927 | A1 | * | 5/2005 | Malek ...................... 623/17.16 |
| 2005/0267470 | A1 | * | 12/2005 | McBride ................... 606/61 |
| 2006/0089646 | A1 | * | 4/2006 | Bonutti ..................... 606/61 |
| 2006/0106381 | A1 | * | 5/2006 | Ferree et al. ............... 606/61 |
| 2006/0235391 | A1 | * | 10/2006 | Sutterlin, III ............ 606/61 |
| 2007/0005062 | A1 | * | 1/2007 | Lange et al. ............... 606/61 |
| 2007/0073293 | A1 | * | 3/2007 | Martz et al. ............... 606/61 |
| 2007/0083200 | A1 | * | 4/2007 | Gittings et al. .............. 606/61 |

* cited by examiner

*Primary Examiner* — Eduardo C Robert
*Assistant Examiner* — Michelle C Eckman
(74) *Attorney, Agent, or Firm* — Gifford, Krass, Sprinkle, Anderson & Citkowski, P.C.

(57) ABSTRACT

Methods for spinal stabilization operative to prevent lateral bending, extension, and rotation across two or more adjacent vertebrae are described with particular emphasis on preventing excessive forces on the facet joins. Broadly, the method includes placing one or more anchors, each having one or more sutures at each vertebral level on a posterior portion of the vertebrae, applying tension to the sutures and joining the sutures over the disc space between two or more vertebra. The sutures can be wrapped around the spinous process of the adjacent vertebrae. Alternatively, the sutures can be welded in a cross-braced pattern extending between the spinous process of the adjacent vertebrae.

24 Claims, 16 Drawing Sheets

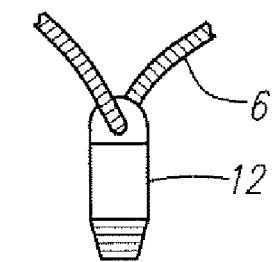
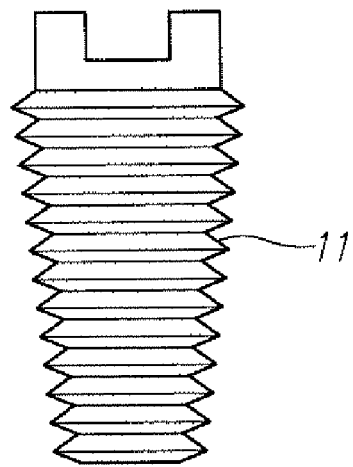
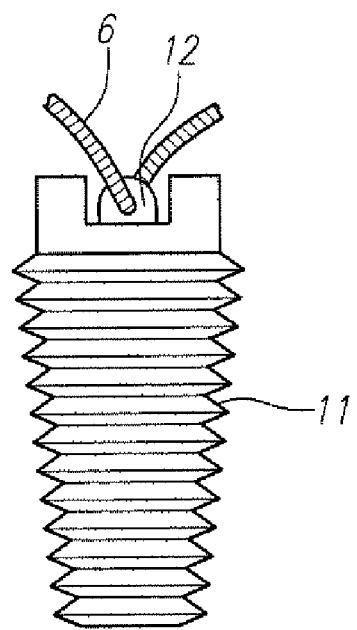
FIG. 10A  FIG. 10B

METHODS OF POSTERIOR FIXATION AND STABILIZATION OF A SPINAL SEGMENT

RELATED APPLICATIONS

This application claims the benefit of provisional application 60/861,499, filed Nov. 28, 2006, entitled "Annulus and Spinal Ligament Reconstruction." This application is related to co-pending application 60/808,795, filed May 26, 2006, entitled "Fastening Assemblies for Disc Herniation Repair and Methods of Use." The application is also related to U.S. Pat. Nos. 6,248,106 and 6,423,065. All of the above-referenced patent and applications are hereby expressly incorporated by reference in their entirety.

FIELD OF THE INVENTION

The subject invention resides in methods and apparatus for stabilizing a spinal segment using one or more fixation members attached to posterior portions of adjacent vertebrae. The invention is particularly well suited to the prevention of excessive spinal motion.

BACKGROUND

The human intervertebral disc is an oval to kidney bean-shaped structure of variable size depending on the location in the spine. The outer portion of the disc is known as the annulus fibrosis (AF). The annulus fibrosis is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The annulus fibrosis contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. This disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the annulus fibrosis. As discussed in co-pending U.S. patent application Ser. No. 10/407,554 and U.S. Pat. No. 6,878,167, the content of each being expressly incorporated herein by reference in their entirety, the posterior portion of the annulus fibrosis has abundant pain fibers.

Herniated nucleus pulposus (HNP) occurs from tears in the annulus fibrosis. The herniated nucleus pulposus often allies pressure on the nerves or spinal cord. Compressed nerves cause back and leg or arm pain. Although a patient's symptoms result primarily from pressure by the nucleus pulposus, the primary pathology Lies in the annulus fibrosis.

Surgery for herniated nucleus pulposus, known as microlumbar diseectomy (MLD), only addresses the nucleus pulposus. The opening in the annulus fibrosis is enlarged during surgery, further weakening the annulus fibrosis. Surgeons also remove generous amounts of the nucleus pulposus to reduce the risk of extruding additional pieces of nucleus pulposus through the defect in the annulus fibrosis. Although microlumbar discectomy decreases or eliminates a patient's leg or arm pain, the procedure damages weakened discs.

SUMMARY

A portion of the anulus fibrosis and a portion of the ligaments of the spine are excised to allow insertion of materials and devices into the disc space. For example, a portion of the anterior half of the anulus fibrosis and a portion of the anterior longitudinal ligament (ALL) are excised to enable insertion of bone growth promoting materials and fusion devices in interbody fusion procedures. Removal of portions of the anulus fibrosis and anterior longitudinal ligament increase the flexibility of the spine and allow excessive motion of the spine. For example, removal of the tissues mentioned permits excessive spinal extension, lateral bending, and axial rotation.

Destabilizing the spine decreases the chance of a successful fusion. The invention may be used to increase the stiffness of the operated segment of the spine. Increasing the stiffness of the spine facilitates spinal fusion.

A portion of the anulus fibrosis and a portion of the anterior longitudinal ligament are also excised to enable insertion of motion preserving devices into the disc. For example, Total Disc Replacements (TDRs) and Nucleus Replacements (NRs) are often inserted through the anterior portion of discs. Excessive spinal extension, lateral bending, and axial rotation following excision of the spinal tissues and insertion of motion preserving devices into the disc space places excessive force on the facets of the spine. Biomechanical studies show the forces across the facets at the operated level of the spine can be doubled by motion preserving devices and the techniques used to insert such devices. Excessive force on the facets may lead to degeneration of the facets. Degeneration of the facets may cause low back pain.

The present invention provides methods for spinal stabilization on the posterior portions of adjacent vertebrae operative to prevent lateral bending, extension, and rotation across a spinal segment with particular emphasis on preventing excessive forces on the facet joints of the spine.

In some embodiments, first and second anchors can be attached across adjacent facets in two adjacent vertebrae. Each anchor has at least one suture passing therethough. The sutures can be passed around the spinous processes of the adjacent vertebrae and joined together to join the two adjacent vertebrae. The sutures can be joined by welding or any other suitable technique known in the art for joining the two ends of a suture. Tension can be applied to the sutures prior to joining to apply compression to the vertebrae and to prevent excessive spinal extension, lateral bending, and axial rotation of the spinal segment thereby reducing the forces placed across the facets. In some embodiments, one or more suture anchors and sutures can also be arranged across anterior portions of the adjacent vertebrae to further apply compression to the vertebrae and to prevent excessive spinal extension, lateral bending, and axial rotation of the spinal segment. The combination of anterior and posterior sutures can also be used to hold an intradiscal device in place between the adjacent vertebrae.

In some embodiments, first and second anchors can be placed on posterior potions of two adjacent vertebrae. The anchors can be placed, for example, in the facets or pedicles of the vertebrae. The anchors placed in the cranial and caudal vertebrae each have at least one elongate member, such as a suture, extending therethrough. Tension is applied to the elongate members and the elongate are attached in the pattern of a figure-eight having left and right generally vertically extending segments and diagonal connections between a spinous process of the first vertebrae and a spinous process of the second vertebrae. In some embodiments, the elongate members on the posterior portions of the vertebrae can also be used to hold an intraspinous device in the interspinous space between two adjacent vertebrae.

In some embodiments, the sutures can be placed in the posterior portions of the vertebrae through one or more minimally invasive openings. One or more minimally invasive surgical openings are made to provide access to the patient's spine. First and second anchors can be placed on posterior potions of two adjacent vertebrae, such as the facets or pedicles, via the minimally invasive openings. Each anchors placed has at least one elongate member, such as a suture, extending therethrough. An introducer sheath or retractor is inserted through one of the one or more minimally invasive surgical openings to access a region between the first anchors on each vertebra and a second introducer sheath through one of the one or more minimally invasive surgical openings to access a region between the second anchors on each vertebra. The elongate members are arranged via the introducer sheaths and then tension is applied to the elongate members and the elongate members are attached in the pattern of a figure-eight having left and right generally vertically extending segments and diagonal connections.

BRIEF DESCRIPTION OF THE DRAWINGS

FIG. 10A is an exploded lateral view of an embodiment of a suture anchor.

FIG. 10B is an exploded lateral view of an alternative embodiment of a suture anchor.

DETAILED DESCRIPTION

Figure 1A:
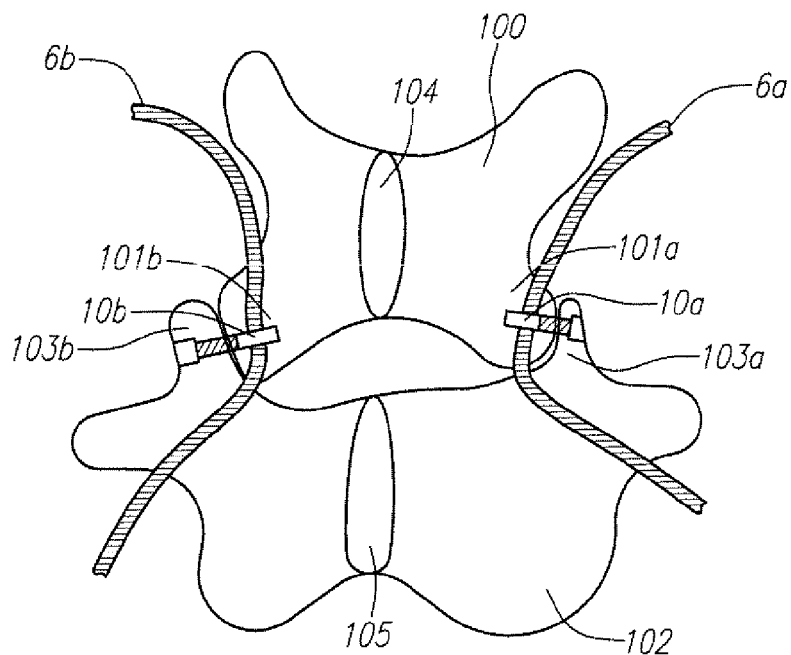
FIG. 1A illustrates a posterior view of segment of a spine with suture anchors placed across the facet joints between two adjacent vertebrae.
Figure 1B:
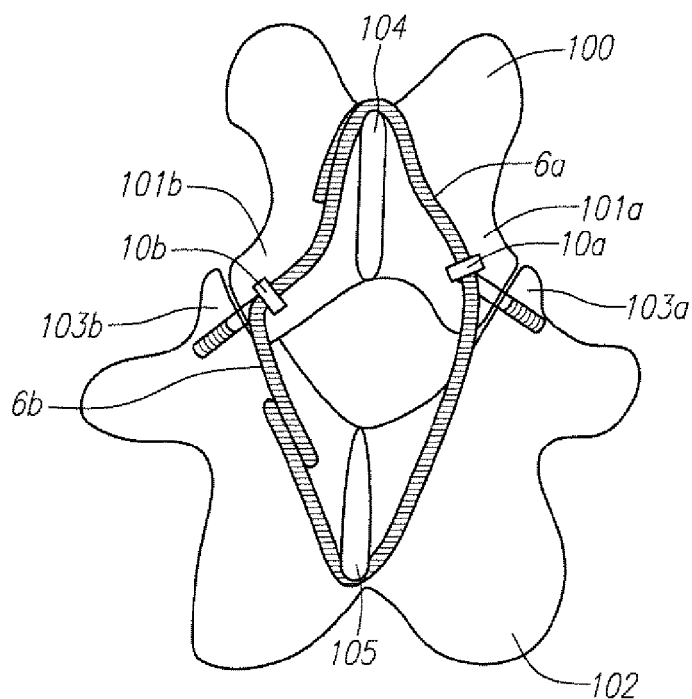
FIG. 1B illustrates a posterior view of the embodiment in FIG. 1A with sutures placed over the spinous processes of the vertebrae and joined together.

FIGS. 1A-1B illustrate a method using two sutures to join adjacent vertebrae across the facet joints to prevent and/or minimize flexion, lateral bending and rotation across a spinal segment with particular emphasis on preventing excessive forces on the facet joints of the spine. As shown in FIG. 1A, suture anchors 10a, 10b are placed across the facet joints 101a,b and 103a,b between the adjacent vertebrae 100 and 102. Each suture anchor 10a,b has at least one eyelet for threading sutures 6a,b. Sutures 6a,b, are threaded through the single eyelets in anchors 10 a,b respectively such that first and second ends of each suture 6a,b extend from anchors 10 a,b.

In some embodiments, the sutures can be monofilament or multifilament configurations of nylon, polypropylene, polyester, polyethylene, or other material. For example in one embodiment, the sutures can be made from a #5 polyester multifilament material. In another embodiment, the sutures can be made of a #5 resorbable multifilament suture such as VICRYL™ (Ethicon, N.J.). In other embodiments, suture materials can be selected for specific characteristics. For example, rigid, semi-rigid or elastic materials may be selected. In embodiments of the invention used in spinal fusion procedures relatively inelastic sutures are preferably used. In other embodiments, the sutures can be made of materials than can be welded together.

As shown in FIG. 1B, the sutures 6a,b are placed around the spinous processes 104, 105 of the adjacent vertebrae and joined together. Tension is applied to the sutures 6a,b prior to joining together to apply compression to the vertebrae 100, 102 and thereby limit spinal flexion, lateral bending, and axial rotation. The ends of sutures 6a,b can be joined together by any suitable method known in the art such as a knot, crimping, melting, welding or otherwise fusing the two ends of the suture. In the illustrated embodiment, the ends of sutures 6a,b are welded together. The weld is preferably caused by heat-generating or heat-conducting instruments. The heat may be generated ultrasonically or by other means. Instruments with special tips may be used to weld the sutures within deep areas of the body. For example, instruments that are about 15 to abut 45 cm in length may be needed to weld sutures in the abdomen or through the muscles in the back. The welding instruments are preferably about 4 to about 8 mm in diameter. In some embodiments, tension can be applied to the sutures 6a,b before the sutures 6a,b are welded together.

Figure 2A:
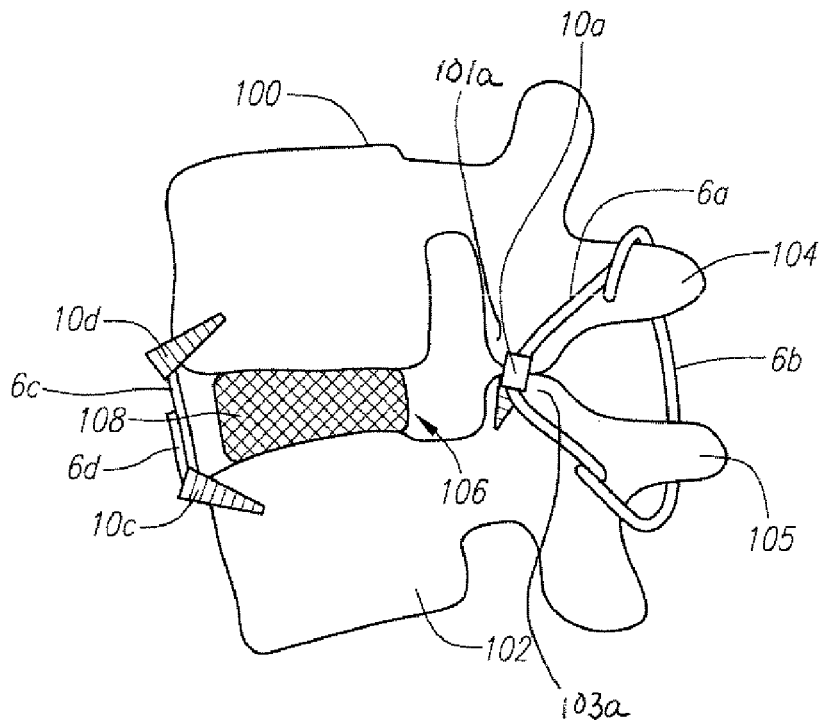
FIG. 2A illustrates a lateral view of an alternative embodiment for stabilizing a spinal segment illustrating both posterior and anterior placed suture stabilization.

In some embodiments, as shown in FIG. 2A, an intradiscal device 108, such as a bone graft or fusion cage can be placed into the disc space 106 between vertebrae 100, 102. The intradiscal device 108 carries the axial load between the vertebrae 100, 102. The intradiscal device 108 also helps limit spinal flexion. The intradiscal device 108 is preferably wedge-shaped and at least as tall as the disc space 106. Such size and shape of the intradiscal device 108 helps to maintain the normal lordosis of the spine despite application of compression to the anterior portion of the spine. Alternatively, the intradiscal device 108 can be wedge-shaped and 1, 2, 3, 4, 5, 6, 7, or more millimeters taller than the disc space. As shown in FIGS. 1A-B and 2A anchor 10a is placed across facets 101a and 103a. Sutures 6a and 6b are threaded through anchors 10a,b, placed around spinous processes 104 and 105. Tension is applied to sutures 6a,b and they are then welded together to maintain the tension and apply compression to vertebrae 100 and 102 and to intradiscal device 108. The tension on the posterior portion of the spine limits spinal flexion, lateral bending, and axial rotation.

Figure 2B:
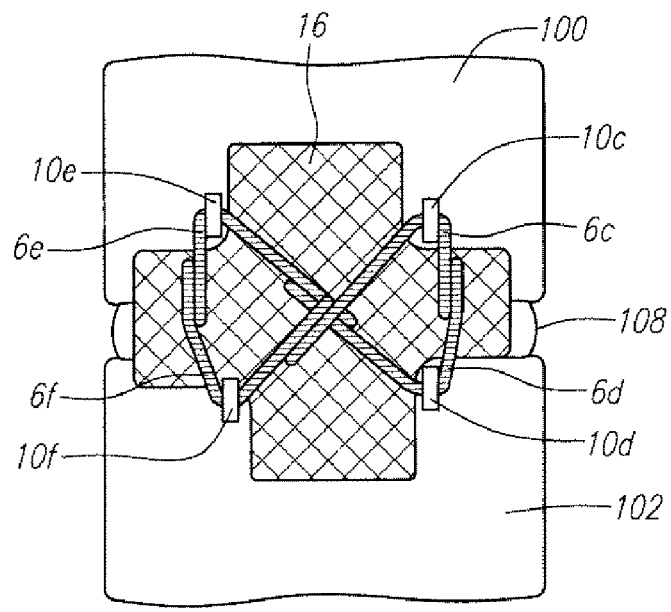
FIG. 2B illustrates an anterior view of the embodiment in FIG. 2A showing sutures on the anterior portion of the vertebrae joined together in a cross-braced pattern.

In addition, in some embodiments, anchors 10c,d,e,f can be placed in the anterior portion of vertebrae 10, 102 and sutures 6c,d,e,f can be threaded through anchors 10c-f and welded together to connect the anterior portions of vertebrae 100, 102 as shown in FIGS. 2A-B and described in more detail in co-pending application entitled "SUTURE WELDING", filed on Nov. 27, 2007, and provisional application 60/861, 499, filed Nov. 28, 2006, entitled "Annulus and Spinal Ligament Reconstruction, all of the which are hereby expressly incorporated by reference in their entirety. Tension is applied to sutures 6c,d,e,f prior to welding to maintain the tension and apply compression to vertebrae 100 and 102 and to intradiscal device 108. The tension on the anterior portion of the spine limits spinal extension, lateral bending, and axial rotation.

Figure 3A:
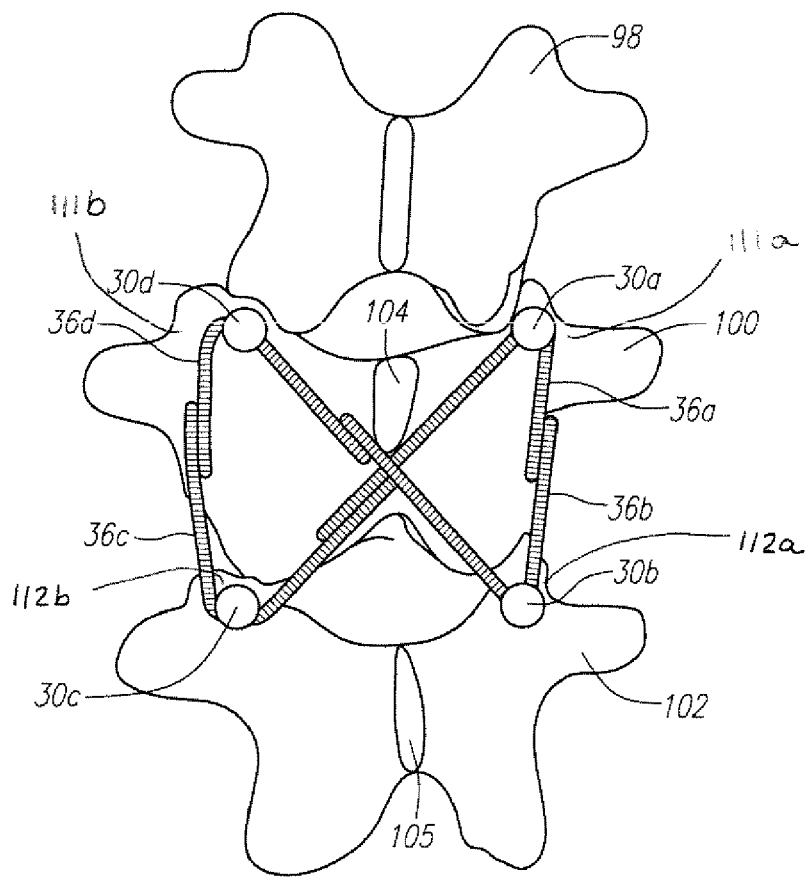
FIG. 3A illustrates a posterior view of a segment of a spine with suture anchors placed in the facet joints of two adjacent vertebrae and sutures joined together in a cross-braced pattern between the spinous processes.
Figure 3B:
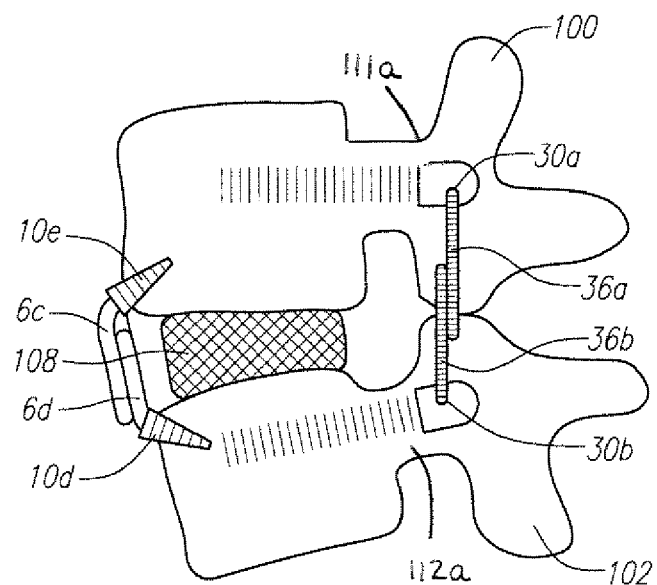
FIG. 3B illustrates a lateral view of a sagittal cross section of the embodiment in FIG. 3A illustrating both posterior and anterior placed suture stabilization.

FIGS. 3A-B illustrates an alternative embodiment of a method for applying sutures to maintain tension on the posterior portion of spine and apply compression to the vertebrae to limit spinal flexion, lateral bending, and axial rotation thereby reducing the forces placed across the facet joints. As shown in FIG. 3A, anchors 30a,b,c,d are placed in pedicles 111a,b and 112a,b of vertebrae 100, 102. In alternative embodiments, the anchors 30a,b,c,d can be placed in other suitable posterior segments of the vertebrae, 100,102 such as the facets. Sutures 36a,b,c,d are threaded through anchors 30a,b,c,d respectively such that first and second ends of each suture 6a,b,c,d extend from anchors 30a,b,c,d.

The medial ends of sutures 36a and 36c and of 36b and 36d are joined in a diagonal, crisscrossed pattern between spinous processes 104, 105 and over the disc space between vertebrae 100 and 102. The lateral ends of the sutures 36a and 36b and of 36c and 36d are likewise joined together to create vertical fixation suture arms. The sutures can be connected using any suitable methods known in the art such as a knot, crimping, melting, welding or otherwise fusing the two ends of the suture. In the illustrated embodiment, tension is applied to sutures and they are then welded together to maintain the tension between and apply compression to the posterior portion of vertebrae 100, 102. The weld is preferably caused by heat-generating or heat-conducting instruments. The heat may be generated ultrasonically or by other means.

This configuration joins the adjacent vertebrae 100 and 102 forms an "X" over the disc space between vertebrae 100 and 102. The vertical and a diagonal configuration of the sutures 36 a,b,c,d over the disc space advantageously provides an arrangement that resists and/or limits flexion, lateral bending and axial rotation.

In some embodiments, as shown in FIG. 3B, an intradiscal device 108 can be inserted into the disc space 106 between vertebrae 100,102 and sutures can be applied to the anterior portion of vertebrae 100, 102 as well to apply tension on the anterior portion of the vertebrae and thereby limit spinal extension, lateral bending, and axial rotation. As shown in FIG. 3B, and discussed above in reference to FIG. 2A, anchors 10c,d,e,f, can be placed in the anterior portion of vertebrae 100, 102 and sutures 6c,d,e,f can be threaded through anchors 10c-f and welded together to connect the anterior portions of vertebrae 100, 102. Tension is applied to sutures 6c,d,e,f prior to welding to maintain the tension between and apply compression to vertebrae 100 and 102 and to intradiscal device 108. Applying tension to both the anterior and posterior portions of vertebrae 100, 102 applies compression to the intradiscal device 108 and vertebrae 100, 102 and limits spinal flexion and extension, lateral bending, and axial rotation. In some embodiments, the sutures 6c-f and 36a-d can be different sizes and/or made of different materials such that the sutures have different tensile strength, elasticity or other properties in order to vary the resistance to the resistance to spinal extension, flexion, lateral bending and axial rotation extension as necessary. For example, in one embodiment, the anteriorly placed sutures 6c-f could be a #5 polyester multifilament material. The posteriorly placed sutures 36a-d could be made of VICRYL™. Alternatively, in some embodiments, one set of sutures could be more elastic than the second set of sutures. For example, one set of sutures 6c-f could reversibly stretch about 1 to about 10 mm. The other set of sutures 36a-d could reversibly stretch about 5 to about 8 mm.

Figure 3C:
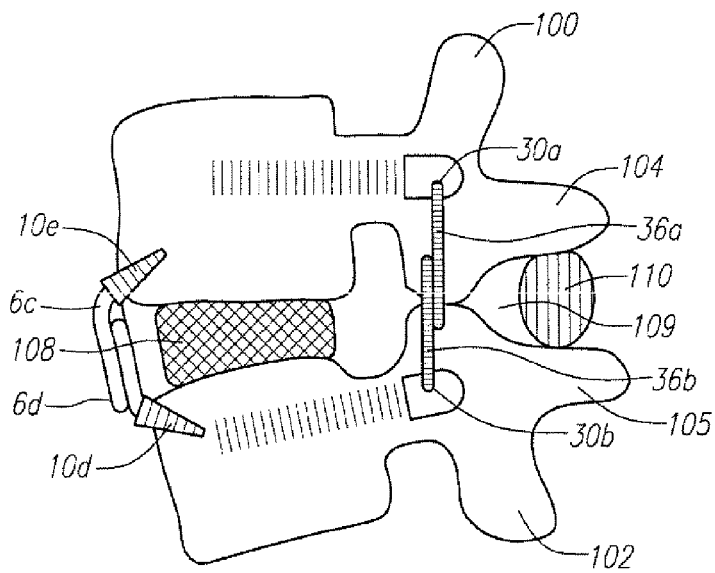
FIG. 3C illustrates a lateral view of a sagittal cross section of the embodiment in FIG. 3B illustrating an interspinous device placed between the spinous processes.

In some embodiments, one or more sutures on the posterior segment of the spine can also be used to hold an intraspinous device in the interspinous space between two adjacent vertebrae. FIG. 3C, is a lateral view of a sagittal cross section of the spine and an alternative embodiment of the invention having an intraspinous device 110 in the interspinous space 109 between spinous processes 104 and 105. The relatively incompressible device carries axial load from one spinous process to the other spinous process. The device could be made of metal (such as titanium, plastic (such as PEEK), bone, an in-situ curing material (such as polymethylmethacrylate (PMMA), bioresorbable materials including in-situ curing materials such as bioactive cements or any other suitable material known in the arts. In one embodiment, the PMMA could be injected into a removable mold. Alternatively, the PMMA could be injected into a second device, such as a bag or tube that was previously placed between the spinous processes. Alternatively, the PMMA could be inserted after curing outside the body. The use of PMMA to stabilize the spine is well known to those skilled in the art.

Figure 3D:
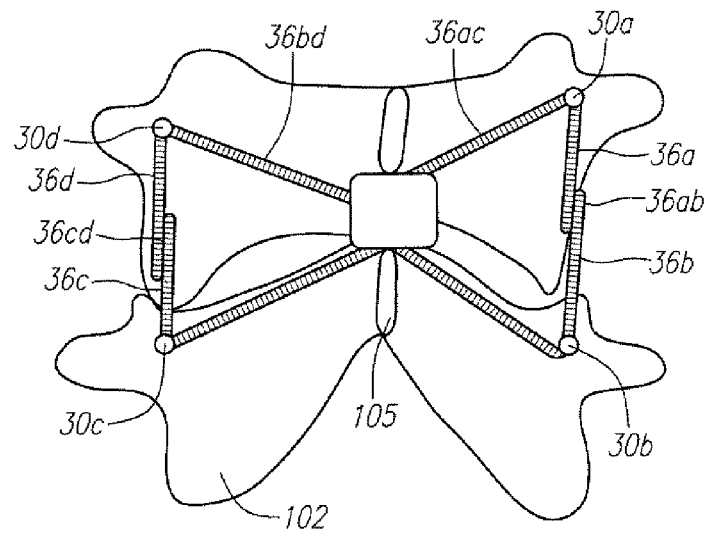
FIG. 3D is posterior view of an alternative embodiment in FIG. 3B illustrating the posterior sutures passing through the interspinous device placed between the spinous processes.

As shown in FIG. 3D, in some embodiments, the diagonal flexible fixation members 36ac and 36bd can be threaded through the intraspinous device 110 between the spinous processes 104 and 105. For example, sutures 36a and 36b can be threaded through device 110 prior to welding suture ends 36a to 36c and 36b to 36d to create the diagonal fixation members 36ac and 36bd. The diagonal fixation members 36ac and 36bd can hold intraspinous device 110 in place between the spinous processes 104 and 105. In some embodiments, tension can be applied to suture ends 36,b,c,d prior to welding such that diagonal fixation members 36ac and 36bd apply tension to the posterior portion of the vertebrae 100 and 102 as well as hold intraspinous device 110 in place.

Figure 3E:
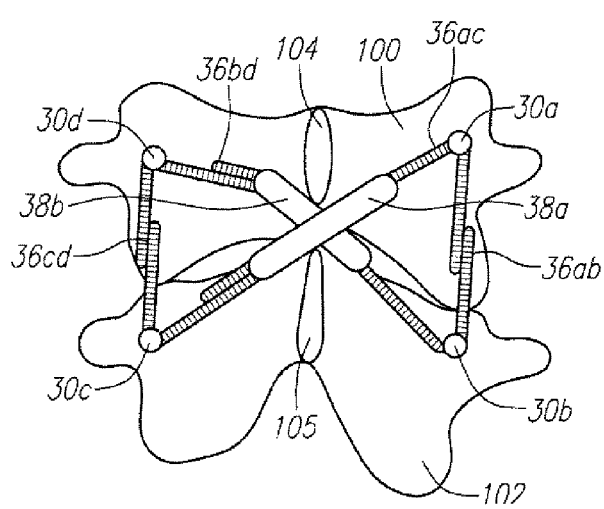
FIG. 3E is posterior view of an alternative embodiment in FIG. 3D illustrating the posterior sutures having sleeves passing between the spinous processes.

In an alternative embodiment, shown in FIG. 3E, the diagonal flexible fixation members 36ac and 36bd are threaded through sleeves 38a and 38b. The sleeves 38a,b are made of relatively incompressible materials. For example, the sleeves can be made of metal (such as titanium, plastic (such as PEEK), bone, an in-situ curing material (such as polymethylmethacrylate (PMMA), bioresorbable materials including in-situ curing materials such as bioactive cements or any other suitable material known in the art. The relatively incompressible sleeves 38a,b carry the axial load from one spinous process to the other spinous process. As discussed above, in some embodiments, tension can be applied to the sutures 36a,b,c,d prior to welding to create tension across diagonal fixation members 36ac and 36bd and limit flexion, lateral bending and axial rotation of the spine.

Percutaneous Posterior Suture Based Stabilization

Figure 4A:
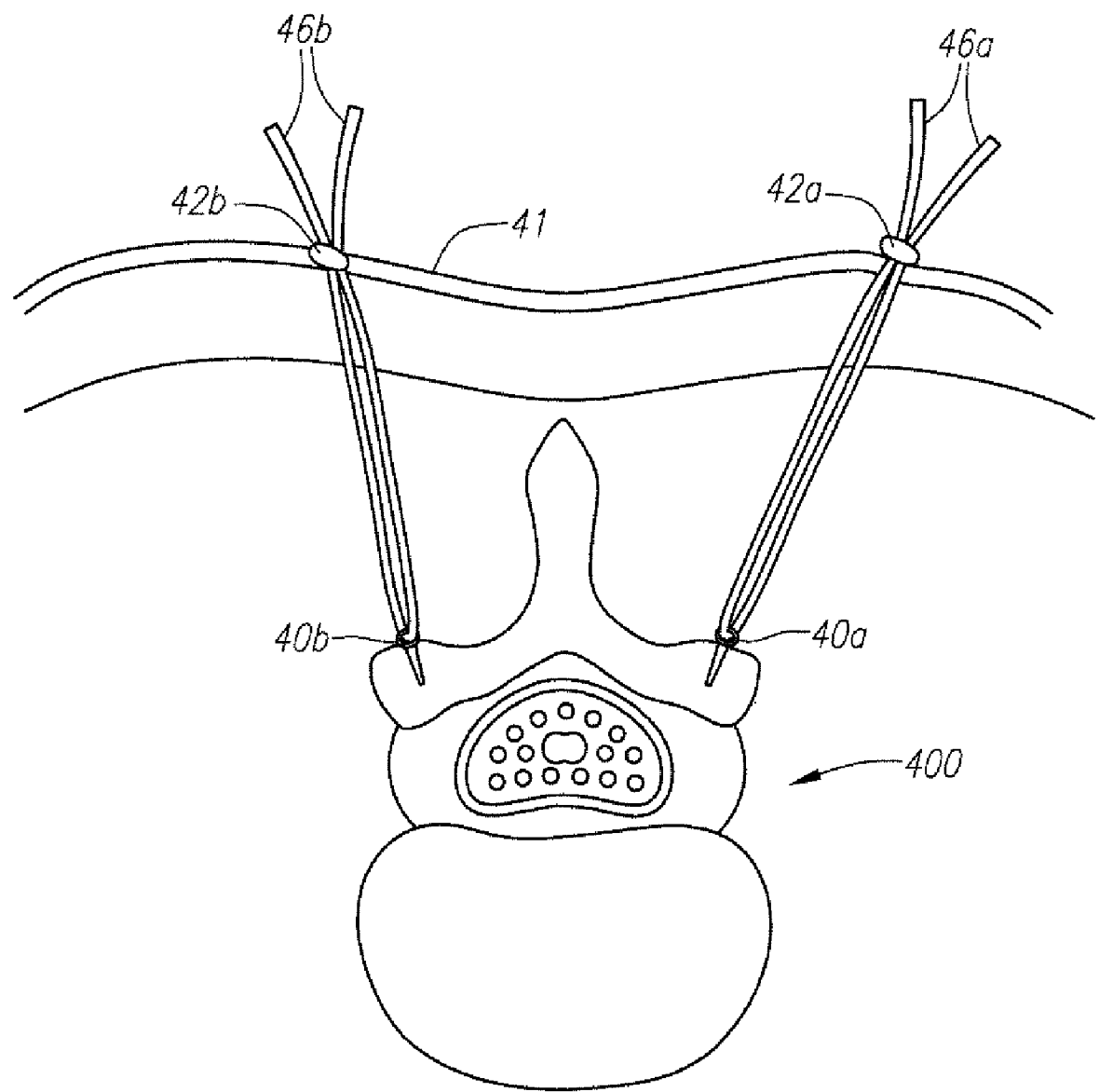
FIG. 4A is a top view of a cross-section of a vertebra illustrating an embodiment of a method for placing sutures in the posterior portions of a spinal segment via minimally invasive openings.
Figure 4B:
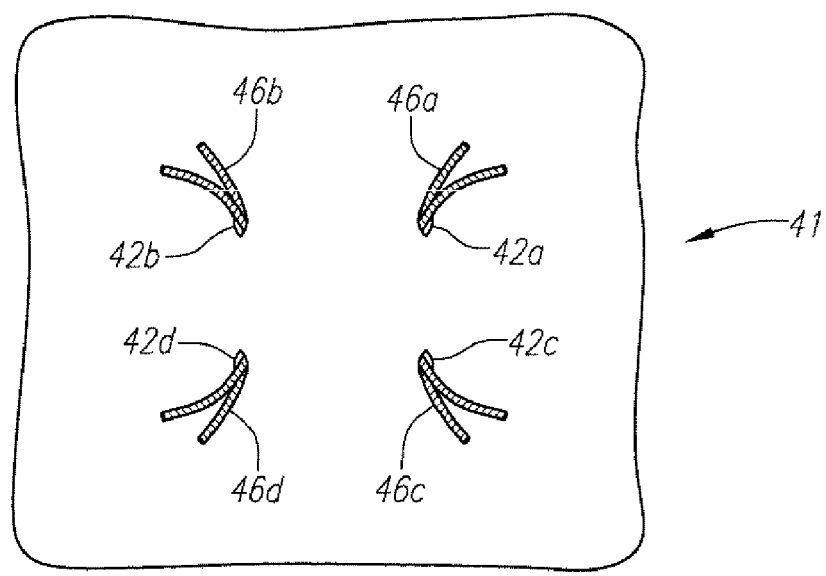
FIG. 4B is a posterior view of the embodiment in FIG. 4A showing four small incisions in a patient's back for placing suture anchors and sutures in two adjacent vertebrae.

In some embodiments, the sutures can be placed in the posterior portions of the vertebrae through one or more minimally invasive openings. As shown in FIGS. 4A-B, one or more minimally invasive surgical openings 42a,b,c,d are made through a patients skin 41 to provide access to the patient's spine. First and second anchors 40a,b are be placed on posterior potions of the vertebrae 400 via the minimally invasive openings 42a,b. Likewise, first and second anchors 40c,d (not shown) are placed on posterior potions of an adjacent vertebrae (not shown) via the minimally invasive openings 42c,d. The minimally invasive openings 42a,b,c,d are preferably less than 6 mm. Alternatively, the incisions could be 4, 5, 6, 7, 8, 9, or more millimeters long. The anchors 40a,b,c,d can be placed into the pedicles of the vertebrae 400, 402, for example as shown in FIGS. 3A and 3B in respect to vertebrae 100, 102. Alternatively, the anchors 40a,b,c,d can be placed in any suitable segment of the posterior portion of the vertebrae such as the facets or the spinous processes.

Each anchor 40a,b,c,d placed has at least one elongate member, such as a sutures 46a,b,c,d, extending therethrough The sutures 46a,b,c,d are seen coursing from the anchors and through the stab wounds. The sutures 46a,b from the cranial set of anchors 40a,b are preferably a different color than the sutures 46c,d in the caudal set of anchors 46c,d.

Figure 4C:
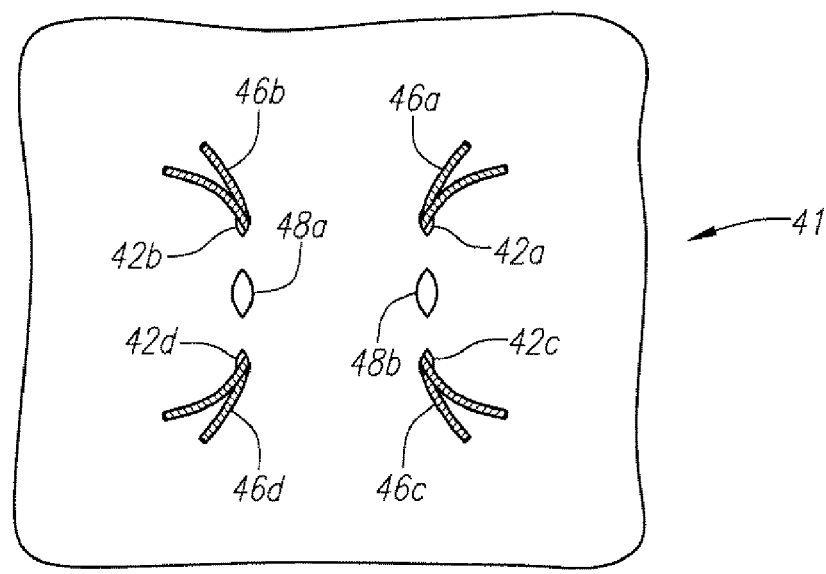
FIG. 4C is a posterior view of the embodiment in FIG. 4B showing two additional incisions between the four original incisions.

As shown in FIG. 4C, two additional incisions 48a and 48b are made between the openings 42a and 42c and 42b and 42d. The incisions 48a and 48b are used to provide access for manipulating the ends of sutures 46a,b,c,d. The incisions are preferably less than 10 mm each. Alternatively, the incisions could be 6, 7, 8, 9, 10, 11, 12, 14, or more millimeters long.

Figure 4D:
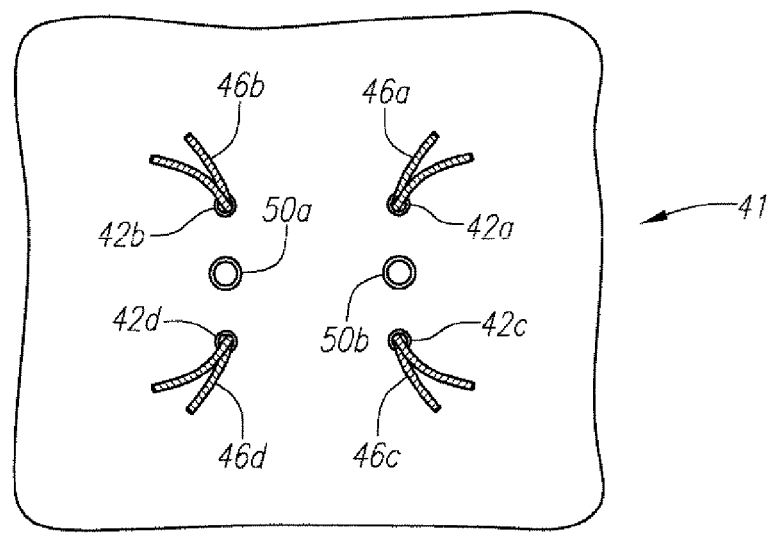
FIG. 4D is a posterior view of the embodiment in FIG. 4C showing retractors placed in the two medial incisions.
Figure 5:
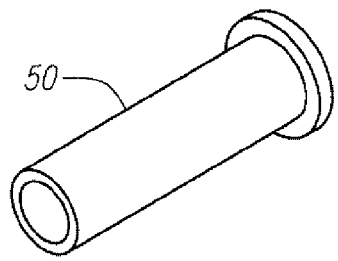
FIG. 5 is an oblique view of a tube-shaped retractor

As shown in FIG. 4D, a first retractor 50a is placed through incisions 44a and a second retractor 50b is placed through incision 48b to hold the incisions 48a,b open and provide a passageway for accessing the sutures 46a,b,c,d at a point close to the suture anchors 40a,b,c,d. As shown in FIG. 5, the retractor 50 has a tubular shape to holds back surrounding tissue and organs, so that the vertebra can be accessed. Alternatively, the retractor could have features that allow expansion of the retractor in-situ to access to the spine. Furthermore, the retractor could have two or more blades that expand rather than a continuous tube.

Figure 6:
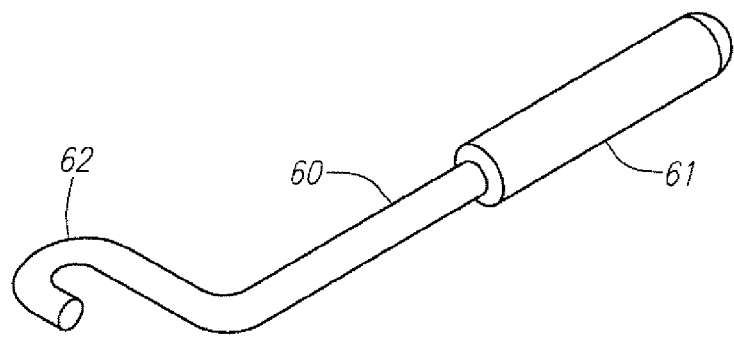
FIG. 6 is an oblique view of a tool for use in the embodiment of the invention drawn in FIGS. 4A-I.
Figure 4E:
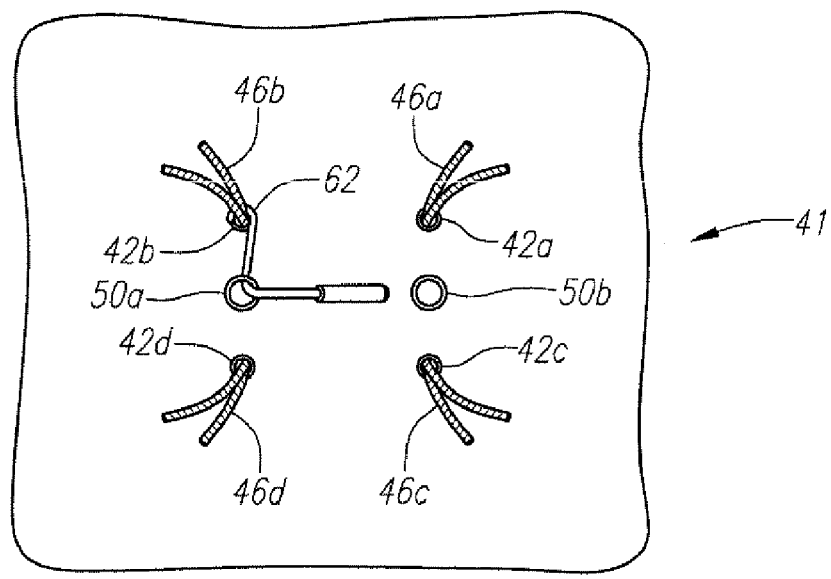
FIG. 4E is a posterior view of the embodiment in FIG. 4D showing the hook end of the instrument drawn in FIG. 7 was passed through the tube retractor, under the skin and through the muscles of the back.
Figure 7:
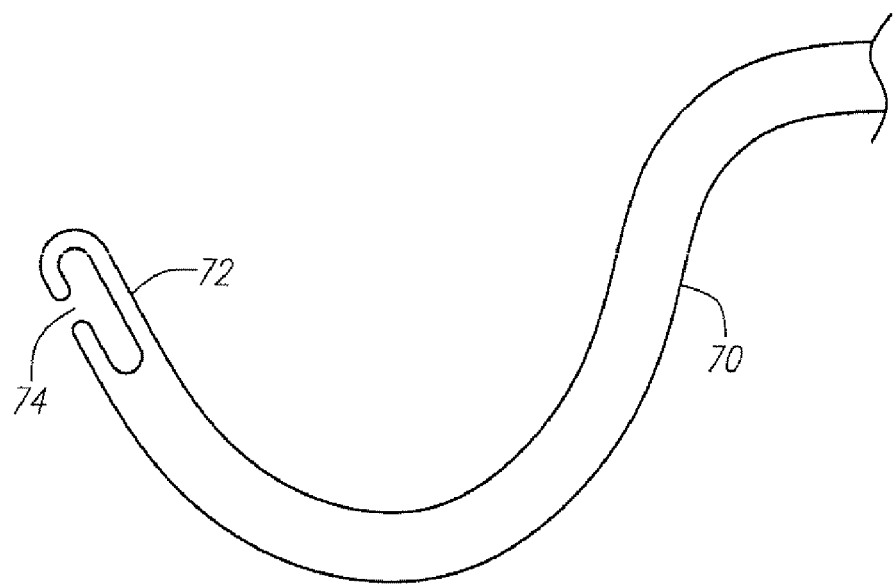
FIG. 7 is a lateral view of an alternative hook shaped tool for use in the embodiment of the invention drawn in FIGS. 4A-I.
Figure 8:
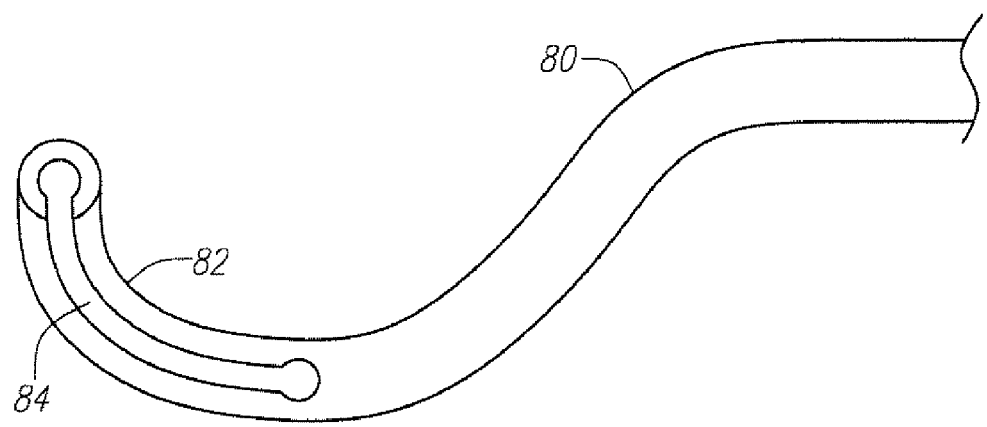
FIG. 8 is a lateral view of an alternative hook shaped tool for use in the embodiment of the invention drawn in FIGS. 4A-I.

As shown in FIG. 4E, a hook shaped tool 60 passed through the tube retractor, under the skin and through the muscles to access the suture 46b at a point close to the anchor 40b (not shown). FIG. 6 is an oblique view of the tool 60 used in the embodiment of the invention drawn in FIG. 4E. The instrument preferably has a hook 62 n one end and a bayonet handle 61 at the opposite end of the tool. In an alternative embodiment as shown in FIG. 7, the tip 72 of the hook shaped tool 70 can have a slot 74 at the end. Alternatively, the tip 82 of the tool 80 can be cannulated 84, as shown in FIG. 8.

The hook shaped end 62 of the tool is used to grasp suture 46b and pull both ends of the suture back through incision 42b, through the muscles and up through retractor 50b. Fluoroscopy may used to help align the hook over the anchor. In some embodiments, the suture may also be manipulated into the hook 62 with a cannulated sleeve over the sutures.

Figure 4F:
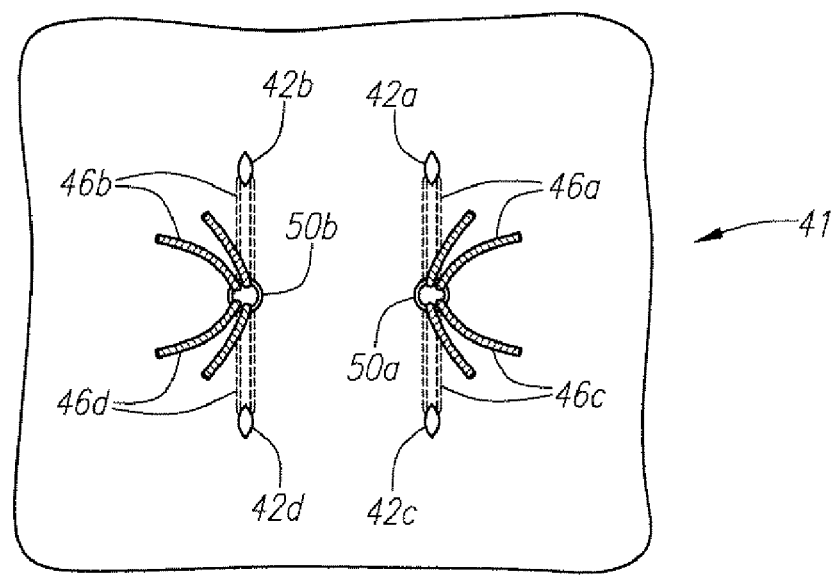
FIG. 4F is a posterior view of the embodiment in FIG. 4E showing ends of the sutures pulled through the retractors with the hook-shaped instrument.

As shown in FIG. 4F, the process is repeated until the ends of each suture 46a,b,c,d have been drawn through the muscles and up through retractors 50a and b. Dotted lines show the path of each suture 46a,b,c,d across the muscle tissue and under the skin to the retractors 50a and b. The ends of the sutures 46a and c are extending from retractors 50a sutures 46b and d extending from retractor 50b can now be joined together.

Figure 4G:
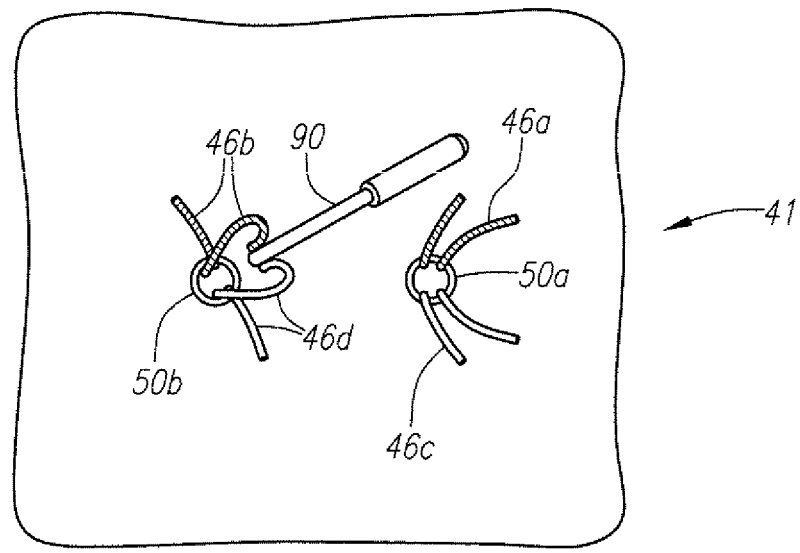
FIG. 4G is a posterior view of the embodiment in FIG. 4F showing a welding tool has been placed over the first ends of a suture from an anchor in the cranial vertebra and a suture from an anchor in the caudal vertebra.
Figure 4H:
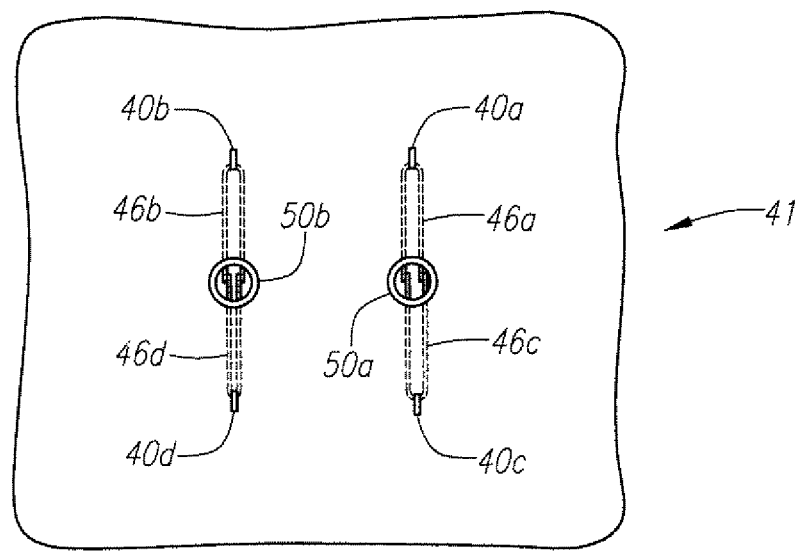
FIG. 4H is a posterior view of the embodiment in FIG. 4G showing the welded ends of the sutures through the two retractors placed in the two medial incisions.
Figure 4I:
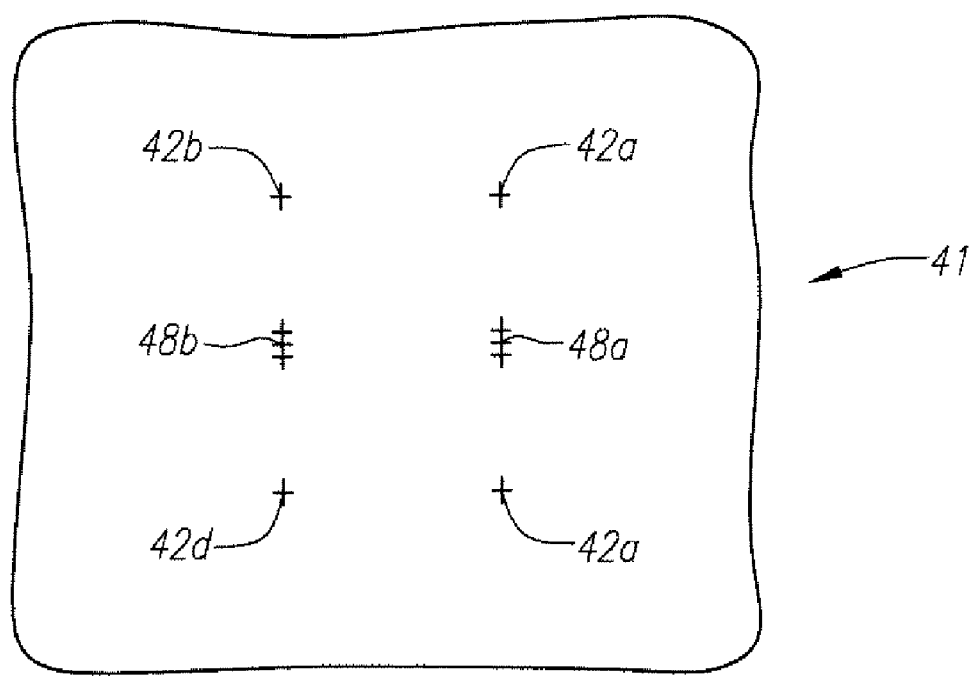
FIG. 4I is a posterior view of the embodiment in FIG. 4G showing the closed incisions.

As shown in FIG. 4G a welding tool 90 has been placed over one end of suture 46b from an anchor in the cranial vertebra one end of suture 46d from an anchor in the caudal vertebra. The tip of the instrument is passed through the retractor sleeve 50b. Tension is applied to the first ends of the sutures 46b and d and the sutures 46b and d are welded together. Fluoroscopy may be used to help guide the tip of the welding tool 90 to the level of the anchors. The process is repeated with the second ends of sutures 46b and d to create a pair of vertical fixation arms 46bd, as shown in FIG. 4H, joining adjacent vertebrae 400 and 402. Similarly, welding tool 70 is placed over first ends of suture 46a and c and passed through the retractor sleeve 50b. Tension is applied to the first ends of the sutures 46a and c and the sutures 46ba and c are welded together. The process is repeated with the second ends of sutures 46a and c to create a second pair of vertical fixation arms 46ac, as shown in FIG. 4H, joining vertebrae 400 and 402. Once the sutures have been welded together, the excess suture is removed, the retractor tubes 50a,b are removed and the incisions 42a,b,e,d and 48a,b are closed as shown in FIG. 4I.

Figure 9A:
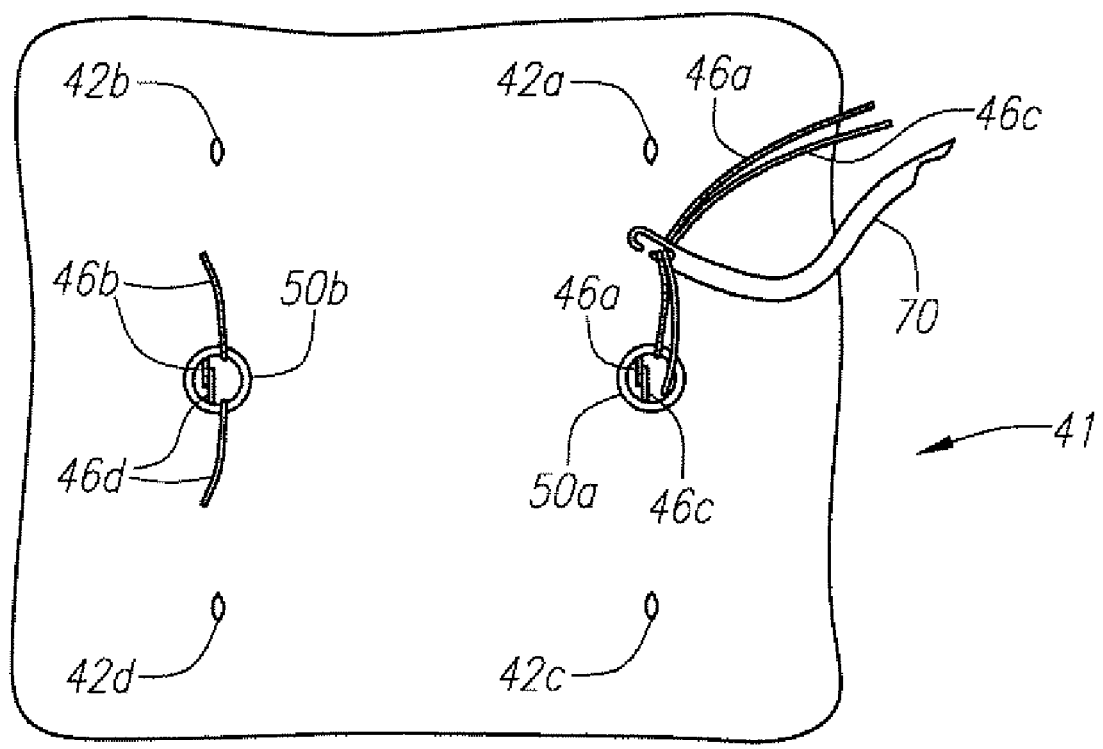
FIG. 9A is posterior view of a portion of patient's back showing second ends of sutures in the cranial and caudal vertebrae pulled through a first retractor with the hook shaped instrument.
Figure 9B:
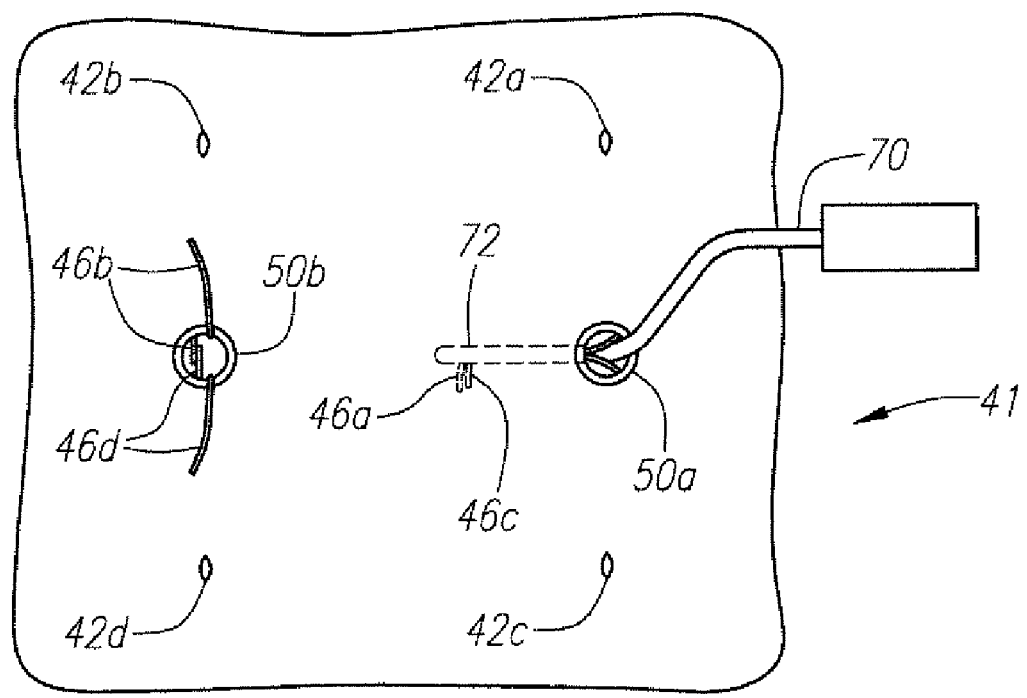
FIG. 9B is a posterior view of the embodiment in FIG. 9A showing the second ends of the sutures passed from a first retractor to the second retractor with the hook-shaped instrument.
Figure 9C:
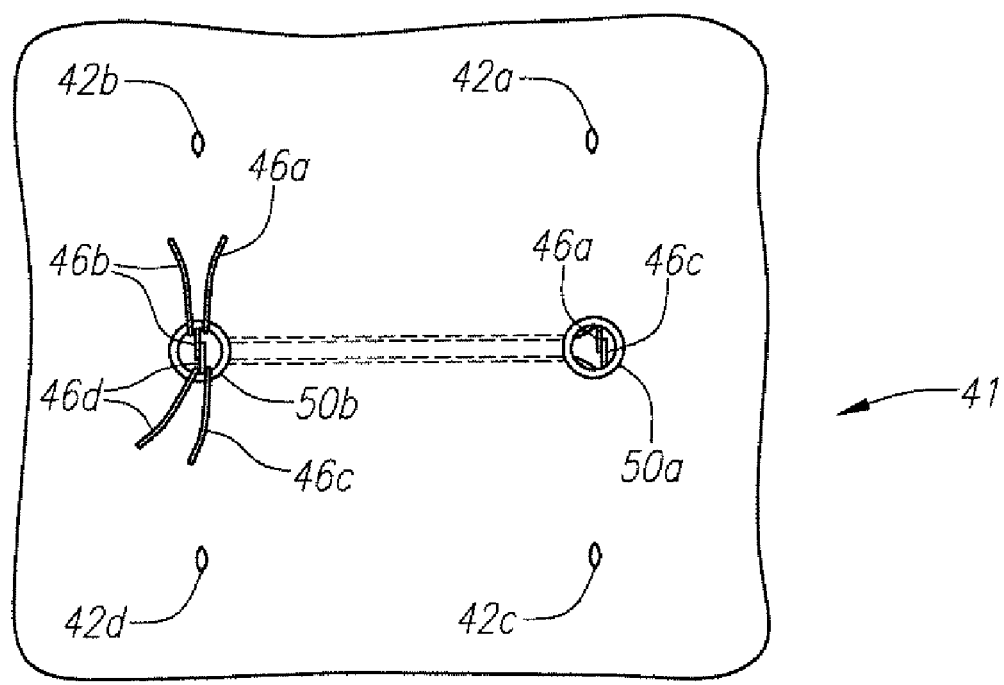
FIG. 9C is a posterior view of the embodiment in FIG. 9B showing the second ends of the sutures pulled through the second retractor.
Figure 9D:
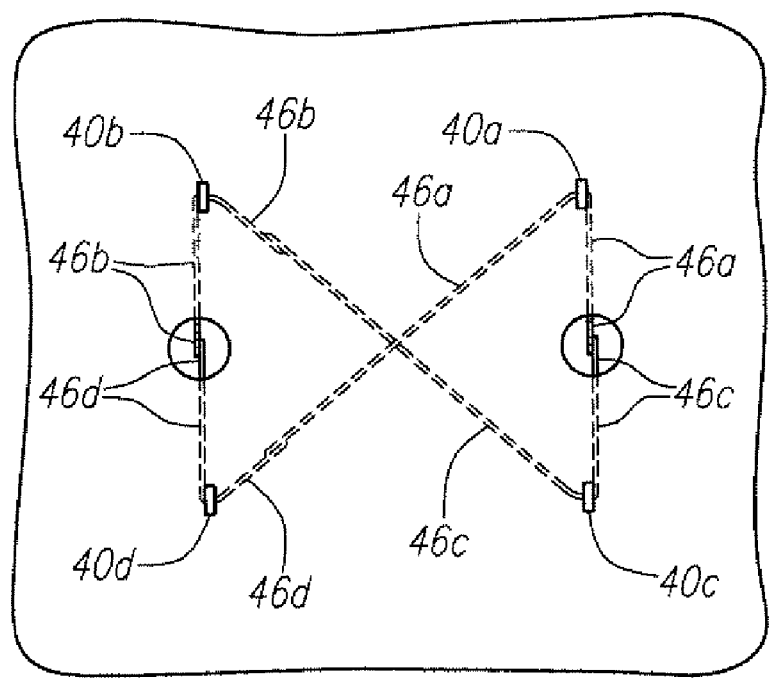
FIG. 9D is a posterior view of the embodiment in FIG. 9C showing the second ends of the sutures joined together in a criss-cross pattern beneath the skin.

In an alternative embodiments, as shown in FIGS. 9A-D the sutures 46a,b,c,d can be arranged in a cross-braced pattern as described in reference to FIG. 3A. Here, as shown in FIG. 9A, the first and second ends of sutures 46a,b,cd are drawn through retractors 50a and b as discussed above with respect to FIGS. 4E-F and the first ends of the sutures 46a and b from the anchors in the cranial vertebrae are welded to the first ends of the sutures 46c and d from the anchors in the in the caudal vertebra to create single vertical fixation arms 46ac and 46bd similar to the process described in FIGS. 4G-4H. The welded portions of the sutures can be seen through the tube retractors 50a,b. However, as shown in FIG. 9A-B, the second ends of the sutures 46a,c from the cranial and caudal anchors on the right side of the spine are grasped by the hook shaped tool 70 and the tool 70 is passed through retractor 50a under the patients skin and up through retractor 50b to thread the second ends of sutures 46a,c from the right side of the spine through retractor 50b on the left side of the spine. The second ends of the sutures 46a and 46d and the second ends of sutures 46b and d are then welded together via a welding tool inserted through the retractor 50b to create diagonal fixation arms 46ad and 46bc.

FIG. 10A is an exploded lateral view of anchor for use in methods of minimally invasive spinal stabilization. The anchor has a first portion 11 for attaching to the vertebra. The first portion 11 is cannulated so that a guide wire can be threaded through the first portion 11 for guiding the anchor to the vertebra through a minimally invasive opening. A second component 12 contains at least one eyelet for threading a suture 6 therethrough. As shown in FIG. 10B, the second component 12 can be fastened to the threaded portion 11 of the anchor after the anchor is inserted into the spine and the guide wire is removed. In some embodiments, the components could be fastened together using shape memory fastening technology. Alternatively, the components could be threaded together or a cam-lock could be used to hold the components together.

Although the foregoing invention has, for the purposes of clarity and understanding, been described in some detail by way of illustration and example, it will be obvious that certain changes and modifications may be practiced which will still fall within the scope of the appended claims.

The invention claimed is:

1. A method for spinal fixation, comprising the steps of:
   providing first and second anchors, wherein each anchor carries a first elongate cable having first and second ends that extend from each anchor;
   attaching the first and second anchors across facets in first and second adjacent vertebrae;
   passing said elongate cables around and in contact with a spinous process of said first vertebra and a spinous process of said second vertebra; and
   securing the first and second ends of the elongate cables to one another.

2. The method of claim 1, further comprising securing the first and second ends of the elongate cables by welding.

3. The method of claim 1, further comprising applying tension to said elongate cables.

4. The method of claim 1, further comprising implanting an intrasdiscal device between said first and second vertebrae.

5. A method for spinal fixation, comprising the steps of:
   providing first, second, third, and fourth anchors, wherein each anchor carries a first elongate cable having first and second ends that extend from each anchor;
   attaching the first anchor to a posterior segment of a first vertebra, attaching the second anchor to a posterior segment of the first vertebra, attaching the third anchor to a posterior segment of a second vertebra, and attaching the fourth anchor to a posterior segment of the second vertebra; and
   attaching each of the first and second ends of the first elongate cable of the first anchor to create an attachment with one of the first and second ends of the first elongate cable of the third and fourth anchors, attaching each of the first and second ends of the first elongate cable of the second anchor to create an attachment with one of the first and second ends of the first elongate cable of the third and fourth anchors,
   wherein the elongate cables are attached in the pattern of a figure-eight having left and right generally vertically extending segments and diagonal connections between a spinous process of the first vertebra and a spinous process of the second vertebra.

6. The method of claim 5, wherein each step of attaching is accomplished by welding.

7. The method of claim 5, wherein the first and second anchors are attached to pedicles of the first vertebrae and the third and fourth anchors are attached to pedicles of the second vertebra.

8. The method of claim 5, wherein the first and second anchors are attached to facets of the first vertebra and the third and fourth anchors are attached to facets of the second vertebra.

9. The method of claim 5, further comprising implanting an interspinous device adapted for placement between the spinous process of the first vertebra and the spinous process of the second vertebra.

10. The method of claim 9, wherein the interspinous device is held in place by one or more elongate cables attached to the posterior segments of the first and second vertebra.

11. The method of claim 10, wherein the one or more of the elongate cables pass through the interspinous device.

12. The method of claim 9, wherein the interspinous device comprises a rigid device composed of a material selected from a group consisting of: metal, plastic, an in situ curing material, bone or a bioabsorbable material.

13. The method of claim 9, wherein the interspinous device comprises a sleeve disposed on one or more elongate cables that pass between the spinous process of the first and second vertebrae.

14. A method for stabilizing a spinal segment, comprising the steps of:
providing first, second, third, and fourth anchors, wherein each anchor carries a first elongate cable having first and second ends that extend from each anchor;
making one or more minimally invasive surgical openings that provide access to the patient's spine;
attaching the first anchor to a first vertebra, attaching the second anchor to the first vertebra, attaching the third anchor to a second vertebra, and attaching the fourth anchor to the second vertebra, wherein all attachments are performed through the one or more minimally invasive surgical openings;
inserting a first introducer sheath through one of the one or more minimally invasive surgical openings to access a region between the first and third anchors;
inserting a second introducer sheath through one of the one or more minimally invasive surgical openings to access a region between the second and fourth anchors; and
attaching each of the first and second ends of the first elongate cable of the first anchor to create an attachment with one of the first and second ends of the first elongate cable of the third and fourth anchors, attaching each of the first and second ends of the first elongate cable of the second anchor to create an attachment with one of the first and second ends of the first elongate cable of the third and fourth anchors.

15. The method of claim 14, wherein each step of attaching is accomplished by welding.

16. The method of claim 14, wherein the elongate cables are attached in the pattern of a figure-eight having left and right generally vertically extending segments and diagonal connections between upper and lower end regions of each vertically extending segment.

17. The method of claim 14, further comprising the step of drawing the first and second ends of the first elongate cable of the first anchor through the first introducer sheath and drawing the first and second ends of the first elongate cable of the third anchor through the first introducer sheath.

18. The method of claim 14, further comprising the step of drawing the first and second ends of the first elongate cable of the second anchor through the second introducer sheath and drawing the first and second ends of the first elongate cable of the fourth anchor through the second introducer sheath.

19. The method of claim 14, wherein the welding is performed through at least one of the first and second introducer sheaths.

20. The method of claim 14, wherein the welding is performed using a welding tool that places the elongate cables under tension.

21. The method of claim 14, wherein one of the first and second ends of the first elongate cable of the first anchor and one of the first and second ends of the first elongate cable of the third anchor are engaged by an elongate instrument inserted through the first introducer sheath and passed through the second introducer sheath.

22. The method of claim 14, wherein one of the first and second ends of the first elongate cable of the second anchor and one of the first and second ends of the first elongate cable of the fourth anchor are engaged by an elongate instrument inserted through the second introducer sheath and passed through the first introducer sheath.

23. The method of claim 14, wherein the first and second ends of the first elongate cable of the first anchor are attached under tension with one of the first and second ends of the first elongate cable of the third and fourth anchors.

24. The method of claim 14, wherein the first and second ends of the first elongate cable of the second anchor are attached under tension with one of the first and second ends of the first elongate cable of the third and fourth anchors.

* * * * *